(12) United States Patent
Pan et al.

(10) Patent No.: US 10,405,802 B2
(45) Date of Patent: Sep. 10, 2019

(54) METHOD FOR DETECTING A HEART RATE

(71) Applicant: WELTREND SEMICONDUCTOR, INC., Hsinchu (TW)

(72) Inventors: Ke-Ning Pan, Hsinchu (TW); Shih-Tsung Kuo, Hsinchu (TW); Chi-Chung Ho, Hsinchu (TW)

(73) Assignee: WELTREND SEMICONDUCTOR, INC., Hsinchu (TW)

( * ) Notice: Subject to any disclaimer, the term of this patent is extended or adjusted under 35 U.S.C. 154(b) by 995 days.

(21) Appl. No.: 14/918,551

(22) Filed: Oct. 20, 2015

(65) Prior Publication Data

US 2016/0317052 A1    Nov. 3, 2016

(30) Foreign Application Priority Data

Apr. 28, 2015    (TW) .............................. 104113599 A

(51) Int. Cl.
*A61B 5/00* (2006.01)
*A61B 5/024* (2006.01)
*A61B 5/1455* (2006.01)
*A61B 5/11* (2006.01)

(52) U.S. Cl.
CPC ............ *A61B 5/7257* (2013.01); *A61B 5/024* (2013.01); *A61B 5/02416* (2013.01); *A61B 5/02438* (2013.01); *A61B 5/14552* (2013.01); *A61B 5/721* (2013.01); *A61B 5/11* (2013.01); *A61B 2562/0219* (2013.01)

(58) Field of Classification Search
CPC .............. A61B 5/7257; A61B 5/14552; A61B 5/02416; A61B 5/024; A61B 5/721; A61B 5/02438; A61B 5/11; A61B 2562/0219
See application file for complete search history.

(56) References Cited

U.S. PATENT DOCUMENTS

2014/0275854 A1 * 9/2014 Venkatraman ......... A61B 5/721
                                                                    600/301
2014/0316305 A1 * 10/2014 Venkatrama .......... A61B 5/1112
                                                                    600/595

* cited by examiner

*Primary Examiner* — Peter Luong
(74) *Attorney, Agent, or Firm* — Hershkovitz & Associates, PLLC; Abe Hershkovitz

(57) ABSTRACT

A method for detecting a heart rate is disclosed and includes: providing a photodetector module, a motion detector and a Fast Fourier Transform (FFT) module; acquiring a first heart rate using the photodetector module and the FFT module; sampling at different time intervals and generating a frame using the motion detector and the FFT module, wherein the frame has a first plurality of peaks and a first plurality of indexes corresponding to the first plurality of peaks, and a plurality of sport intervals are defined by the first plurality of indexes; and acquiring a present heart rate by applying an interval tracking algorithm to the first heart rate and the plurality of sport intervals generated from the sampling at different time intervals.

20 Claims, 9 Drawing Sheets

METHOD FOR DETECTING A HEART RATE

CROSS-REFERENCE TO RELATED APPLICATION AND CLAIM OF PRIORITY

This application claims the benefit of Taiwan Patent Application No. 104113599, filed on Apr. 28, 2015, at the Taiwan Intellectual Property Office, the disclosures of which are incorporated herein in their entirety by reference.

FIELD OF THE INVENTION

The present invention relates to a method for detecting a heart rate, and more particularly to a method for detecting a heart rate during exercise.

BACKGROUND OF THE INVENTION

In conventional applications, biosensors for detecting the physiological signals are applied in large medical equipment. However, with new technical developments, wearable devices which were originally applied for medical purposes can also be the ones for the purposes of health and fitness. Because the market for wearable devices is growing, the application of biosensors to wearable devices has attracted more and more attention.

In the prior art, the method for detecting a heart rate in a wearable device is to measure the signal for the change of the vessel volume, and this signal is measured by recording and sensing the energy variation of light using photoplethysmography (PPG). Because the heart beats are periodically verified, the volume of the blood flow in the vessels per unit of cross-sectional area will change periodically. When the volume of the blood flow per unit of cross-sectional area changes, voltage signals, current signals or resistance signals will be detected by a photodetector with the variation of the volume of the blood flow. The relevant conventional techniques are described in patent applications such as CN103156591, WO2013038296, U.S. Pat. No. 8,172,761, US20090112111 and U.S. Pat. No. 5,807,267, and IEEE literature such as Hayato Fukushima et al. "Estimating Heart Rate using Wrist-type Photoplethysmography and Acceleration sensor while running" (Engineering in Medicine and Biology Society (EMBC), 2012 Annual International Conference of the IEEE, Aug. 28, 2012, p. 2901-2904.) and Zhilin Zhang et al. "A General Framework for Heart Rate Monitoring Using Wrist-Type Photoplethysmography (PPG) Signals During Intensive Physical Exercise" (IEEE Transactions on Biomedical Engineering, February 2015, 62(2): 522-531.), and a thesis such as Bennett Ames Fallow "Influence of Skin Type and wavelength on Light Wave Reflectance" (Master Thesis of Science in Kinesiology, the University of Texas at Austin, May 2012.).

However, the signals detected by the photodector may be interfered with and there is substantial noise in the signal because of the human body's motions during exercise, which causes serious distortion of the detected heart rate. Even in a motionless situation, static activities such as pressing the keys of a keyboard or writing also cause the distortion of the detected heart rate.

To overcome the drawbacks in the prior art, a method for detecting a heart rate is disclosed. The particular design in the present invention not only deals with the problems described above, but is also easily implemented. Thus, the present invention has utility for the industry.

SUMMARY OF THE INVENTION

In accordance with one aspect of the present invention, a method for detecting a heart rate is disclosed. The method for detecting a heart rate includes providing a photodetector module, a motion detector and a Fast Fourier Transform (FFT) module; acquiring a first heart rate by using the photodetector module and the FFT module; sampling at different time intervals and generating a frame using the motion detector and the FFT module, wherein the frame has a first plurality of peaks and a first plurality of indexes corresponding to the first plurality of peaks, and a plurality of sport intervals are defined by the first plurality of indexes; and acquiring a present heart rate by applying an interval tracking algorithm with the first heart rate and the plurality of sport intervals generated from the sampling at different time intervals.

In accordance with another aspect of the present invention, a method for detecting a heart rate is disclosed. The method for detecting a heart rate includes acquiring a motion signal of a sporter; acquiring a first heart rate from a first heart rate spectrum of the sporter at a first time interval and a second heart rate spectrum of the sporter at a second time interval, wherein the second heart rate spectrum has a first plurality of peaks and a first plurality of indexes corresponding to the first plurality of peaks; acquiring a frame of the motion signal at the second time interval, wherein the frame has a second plurality of peaks; defining the second plurality of peaks with a second plurality of indexes, and marking a first position corresponding to the first heart rate; and selecting a peak from the first plurality of peaks corresponding to a plurality of positions of the second plurality of indexes as a second heart rate, wherein the peak has a specific mathematical relationship with the first position.

In accordance with another aspect of the present invention, a method for detecting a heart rate is disclosed. The method for detecting a heart rate includes acquiring a first heart rate from a first heart rate spectrum of a sporter at a first time interval and a second heart rate spectrum of the sporter at a second time interval, wherein the second heart rate spectrum has a first plurality of peaks and a first plurality of indexes corresponding to the first plurality of peaks; marking the first heart rate in a first position of a first plurality of frequency intervals; and selecting a specific peak from the first plurality of peaks, which has a specific mathematical relationship with the first position, and is a second heart rate.

BRIEF DESCRIPTION OF THE DRAWINGS

The above objects and advantages of the present invention will become more readily apparent to those ordinarily skilled in the art after reviewing the following detailed descriptions and accompanying drawings.

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 1:
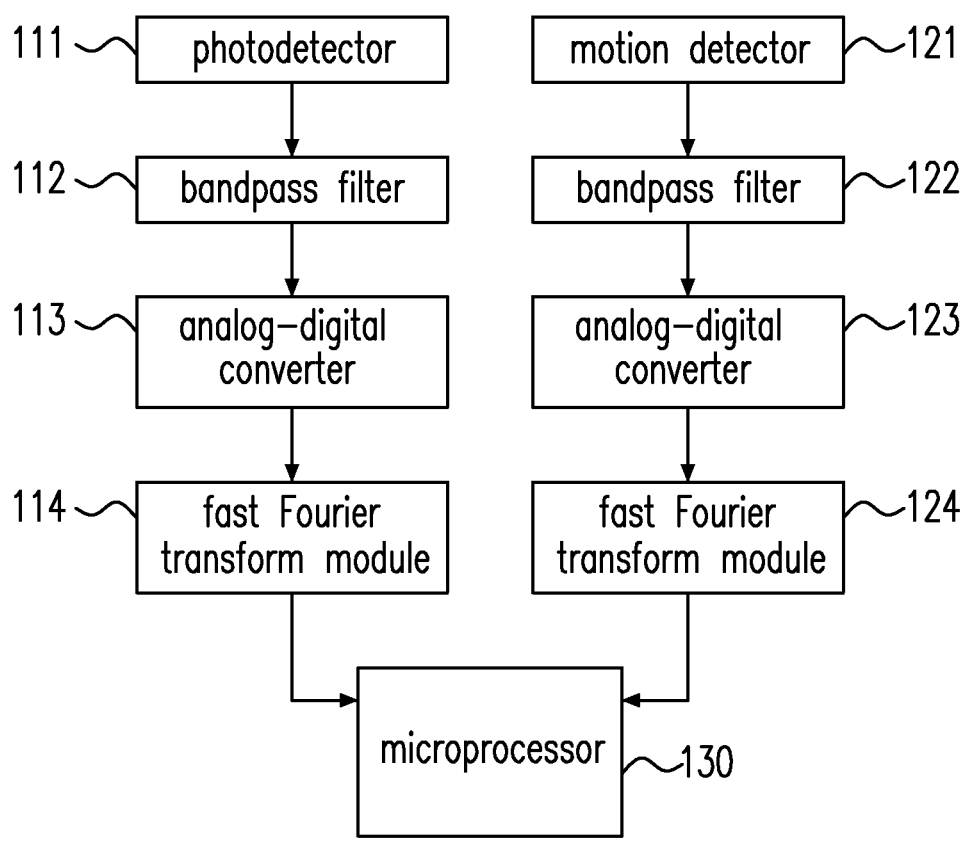
FIG. 1 is a diagram showing a system for detecting a heart rate according to a first embodiment in the present invention.

Please refer to FIG. 1, which is a diagram showing a system 10 for detecting a heart rate according to a first embodiment in the present invention. The system 10 includes a photodetector 111, a motion detector 121, band-pass filters (BPF) 112 and 122, analog-digital converters (ADC) 113 and 123, fast Fourier transform (FFT) modules 114 and 124, and a micro processor 130.

Figure 2:
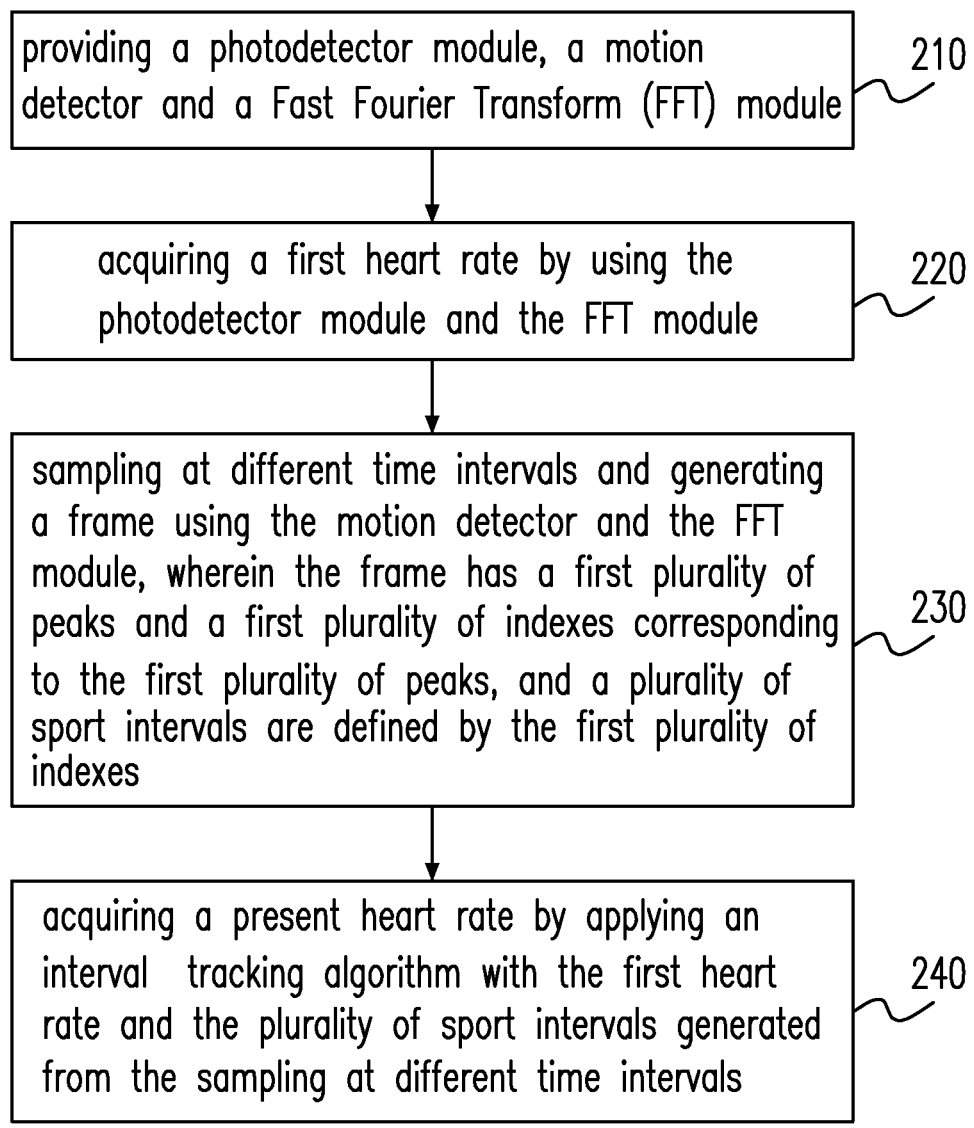
FIG. 2 is a flow chart of detecting a heart rate according to the first embodiment in the present invention.
Figure 3:
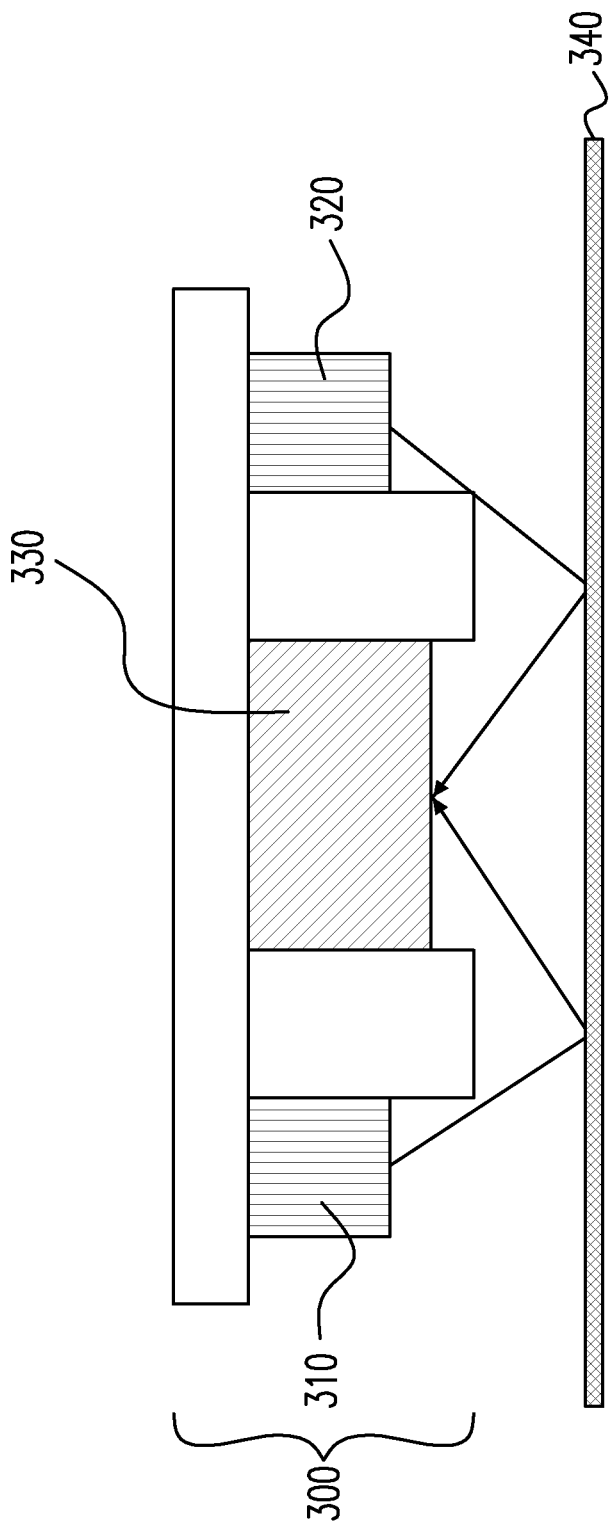
FIG. 3 is a schematic diagram of acquiring signals of a photodetector using a photodetector module according to the first embodiment in the present invention.

Please refer to FIG. 2, which is a flow chart of detecting a heart rate according to the first embodiment in the present invention. In step 210 of the method 20, a photodetector 111, a motion detector 121 and FFT modules 114 and 124 are provided. Please refer to FIG. 3, which is a schematic diagram of acquiring signals of a photodetector using a photodetector module 300 according to the first embodiment. After the light beams of the light sources 310 and 320 are illuminated to the vessel 340 in the corium layer, the photodetector 330 receives the reflected light and converts a light signal from the reflected light to an analog signal. Preferably, the photodetector 330 is the TSL-12T Light-to-Voltage Convertor produced by the AMS Corporation (Austria). The photodetector 330 converts the harvested reflected light signals to voltage signals, so as to obtain a PPG diagram. The reflectance and the signal-to-noise ratio (SNR) of light depend on the wavelength of the light and the skin color illuminated by the light, and the SNRs with regard to different skin colors are verified during exercise. In a rest condition, the SNR and the reflectance of green light (wavelength=525 nm) illuminating various skin colors is better than in other wavelengths. The SNR of blue light (wavelength=470 nm) illuminating both light and dark skin colors has better performance during exercise. Therefore, a combined light originating from a blue LED 310 and a green LED 320 is used in the first embodiment to compensate the SNR difference for different skin colors.

A skilled person in the art can understand that the range of a human heart rate is within a frequency range of 0.5 Hz to 4 Hz. According to the Nyquist sampling theorem, the sampling rate must be more than 8 Hz, and thus the sampling rate is 16 Hz in this embodiment. Because the digital signal in the FFT must be $2^N$ points, where N is a positive integer larger than 1, N=8 is selected in this embodiment. That is, there are data from 256 points in a frame, and the recording time (T) is 16 seconds. After the FFT calculation, 0 to 255 indexes corresponding to the digital signal of the 256 points are obtained, wherein the frequency energies at indexes 0 to 127 and indexes 128 to 255 are the same, and thus only indexes 0 to 127 are used. In addition, because $\Delta = 1/T = 0.0625$ Hz, the relationship between the index and the frequency is: index 0=0 Hz, index 1=0.0625 Hz, index 2=0.125 Hz, index 3=0.1875 Hz, . . . and index 127=7.9375 Hz. Furthermore, to simplify the illustration in the drawings, only the frequency unit is presented at the x-axis in FIGS. 4, 5, 8(*a*) and 8(*b*) (see below), and it is understood that the frequency unit at the x-axis also corresponds to the index unit according to the above-mentioned relationship between the index and the frequency.

Figure 4:
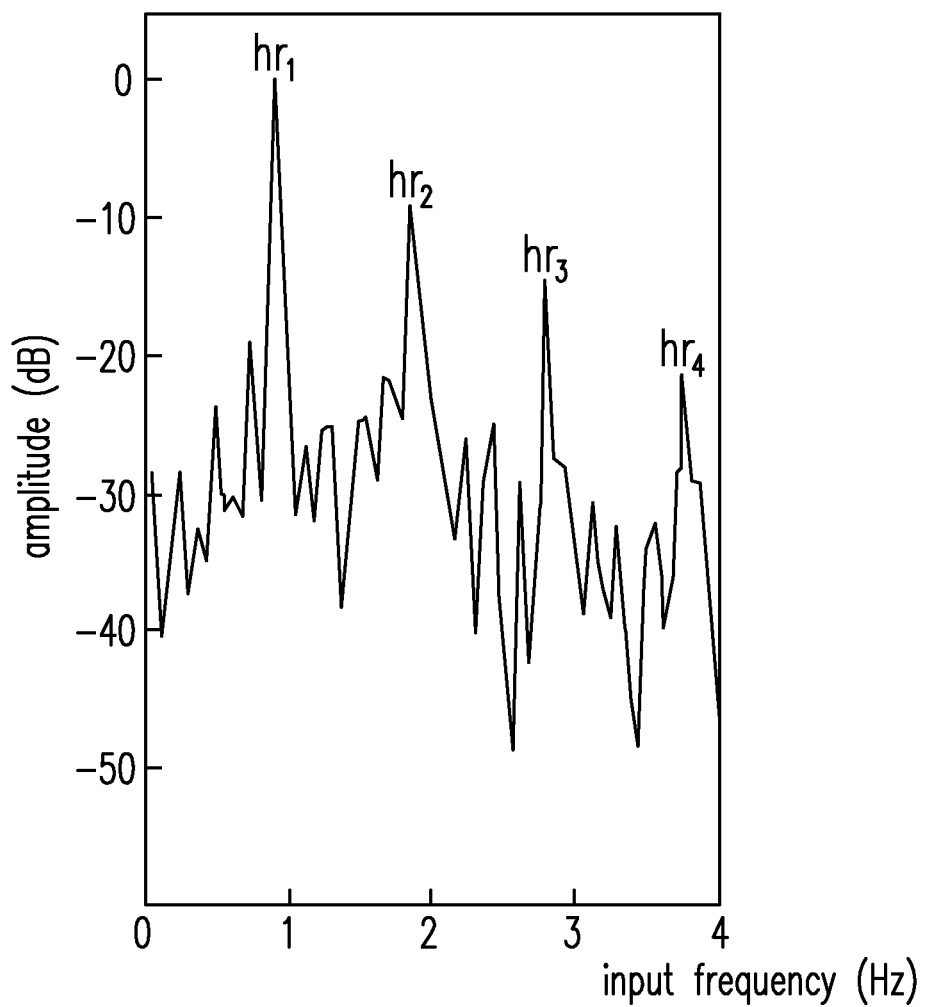
FIG. 4 is a spectral distribution of the signals of the photodetector according to the first embodiment in the present invention.

Please refer to FIGS. 1, 2 and 4. In step 220 of the system 20 in FIG. 2, a first heart rate is obtained using the photodetector module and the FFT module. Because a human heart rate is in a range of 30 to 240 heart beats per minute, which corresponds to a frequency of 0.5 Hz to 4 Hz, the signal obtained from the photodetector 111 is filtered using a BPF 112 at the frequency of 0.5 Hz to 4 Hz to remove any noise. The filtered signal is subsequently converted to the digital signal using the ADC 113. As described in the previous paragraph, the digital signal of 256 points is obtained after sampling for 16 seconds (T=16 seconds). By performing the FFT calculation for the digital signal using the FFT module 114, the spectral distribution of the PPG is acquired. The acquired data are transmitted to the microprocessor 130 to obtain a frame having a plurality of indexes corresponding to a plurality of peaks, and then the plurality of indexes are arranged according to their amplitudes. Several top arranged indexes are combined into a set of HR'=$hr_i$. The signals/data converted by the ADC 113 are successively generated over time, and old data will be overwritten by the newly-generated data. When all or part of the old data are updated, the FFT are performed to obtain a new frame and a new HR' set. FIG. 4 shows a FFT distribution of the PPG for a human at rest, and his/her PPG signal is a harmonic signal which includes a fundamental frequency and a plurality of harmonic frequencies. Preferably, the top four indexes of the HR' set are selected, i.e. HR'=$hr_1, hr_2, hr_3, hr_4$, wherein the frequency corresponding to $hr_1$ is the present heart rate (a first heart rate).

Figure 5:
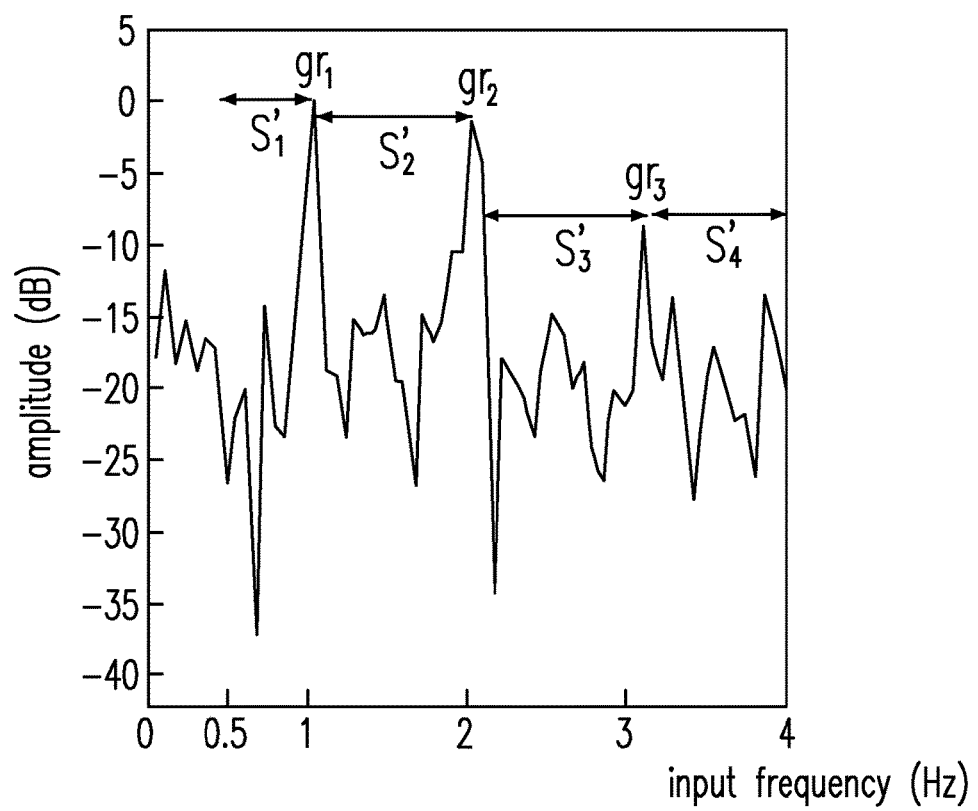
FIG. 5 is a spectral distribution of motion signals according to the first embodiment in the present invention.

Please refer to FIGS. 1, 2 and 5. In step 230 of the system in FIG. 2, a frame is generated using the motion detector and the FFT module at the different time intervals, wherein the frame has a plurality of peaks and a first plurality of indexes corresponding to the plurality of peaks, and a plurality of sport intervals are defined by the first plurality of indexes. When the human starts to move or exercise, the motion signals are obtained using a motion detector 121. A tri-axis accelerometer (hereinafter abbreviated as "G-sensor") is used as the motion detector in this embodiment, and preferably is the KXTJ2-1009 tri-axis accelerometer produced by Kionix Corporation (Ithaca, N.Y., U.S.A.). The motion signals are transmitted to a micro-control unit (MCU) via the fast-mode I²C and filtered using the BPF 122. The sampling frequency of the motion detector 121 is the integral multiple to that of the ADC 123, but the sampling period of the motion detector 121 is the same as that of the ADC 123. The 256 points of data for the G-sensor are obtained after T=16 seconds, and the spectral distribution of the data is calculated by the FFT module 124. The obtained data are transmitted to the microprocessor 130, and the result is shown in FIG. 5. The sport index $gr_1$ corresponding to the peak with the largest energy, the sport index $gr_2$ corresponding to the peak with the second largest energy, the sport index $gr_3$ corresponding to the peak with the third largest energy, and so on, are determined from a range of the $index_{min}$ (index=8) corresponding to 0.5 Hz to the $index_{max}$ (index=64) corresponding to 4 Hz. A GR' set is defined as the set of the sport indexes. The motion signal at the condition of the regular motion (such as walking with two arms swinging naturally or jogging) is a harmonic signal which includes a fundamental frequency and a plurality of harmonic frequencies, and thus there are multiple between the sport indexes. The top three sport indexes (i.e. GR'=$gr_1$, $gr_2$, $gr_3$) are taken as examples in this embodiment, and the equation (1) is established as follows.

$$\begin{cases} gr2 = (gr1 \times 2) \pm 1 \\ gr3 = (gr1 \times 3) \pm 2 \end{cases} \quad (1)$$

If the equation (1) cannot be established, it means that the human body is in the rest mode, that is, GR'={ø}. As shown in FIG. 5, when GR'={ø}, the indexes of the index set in the n+1 sport intervals can be determined by the n elements in the range from $index_{min}$ to $index_{max}$ of the GR' set. The set $S_1'$ is the index set having indexes from $index_{min}$ to $gr_1$, the set $S_2'$ is the index set having indexes from $gr_1+1$ to $gr_2$, the set $S_3'$ is the index set having indexes from $gr_2+1$ to $gr_3$, the set $S_4'$ is the index set having indexes from $gr_3+1$ to $index_{max}$, and S={S1' S2' S3' S4'}.

Figure 6:
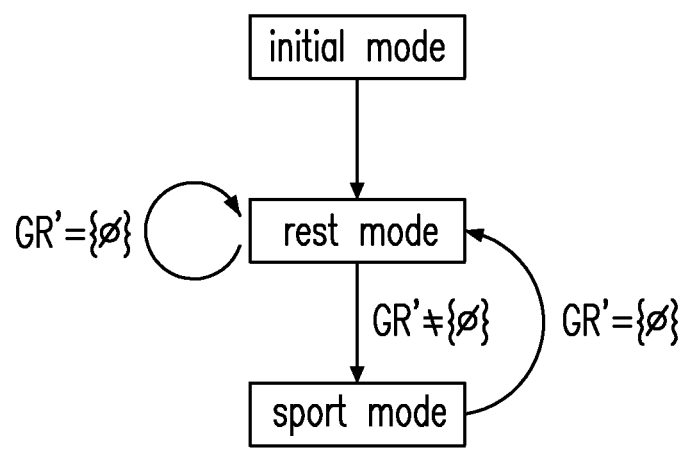
FIG. 6 is a schematic diagram of determining an activity mode of a human body according to the first embodiment in the present invention.

Please refer to FIG. 6, which is a schematic diagram of determining an activity mode of a human body according to the first embodiment in the present invention. In this embodiment, the activity mode of the human body is divided into an initial mode, a rest mode and a sport mode using the G-sensor. When a new frame is generated, the mode is switched among these three modes according to the signals received by the G-sensor:

1. The initial mode: The measurement of the heart rate can be performed only when the user is in the rest condition. The ADC data of $2^N$ points are obtained after T seconds, and the HR' set is calculated by the FFT, wherein $hr_1$ is the index of the present heart rate ($hr_L$).

2. The rest mode: When GR'={ø}, it means that the user is in the static condition or a slight motion condition.

Figure 7:
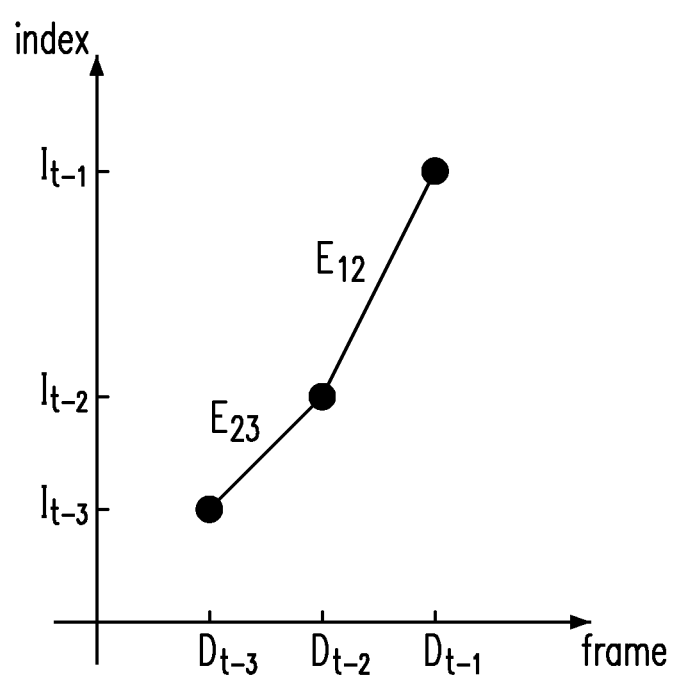
FIG. 7 is a diagram showing the time versus heart rate according to the first embodiment in the present invention.

3. The sport mode: When GR'≠{ø}, it means that the user is doing regular sports. As shown in FIG. 7, the index of the heart rate before three frames ($D_{t-3}$) is recorded as $I_{t-3}$, the index of the heart rate before two frames ($D_{t-2}$) is recorded as $I_{t-2}$, and the index of the heart rate before one frame ($D_{t-1}$) is recorded as $I_{t-1}$, wherein the index $I_{t-1}$ is also the index of the previous heart rate ($hr_P$). Equation (2) is used to calculate the slope $E_{23}$ from $D_{t-3}$ to $D_{t-2}$ and the slope $E_{12}$ from $D_{t-2}$ to $D_{t-1}$.

$$E_{23} = \frac{I_{t-2} - I_{t-3}}{D_{t-2} - D_{t-3}}, E_{12} = \frac{I_{t-1} - I_{t-2}}{D_{t-1} - D_{t-2}} \quad (2)$$

The following are the detailed descriptions for these three modes.

The initial mode: Because the user is in the rest condition, the signals received by the photodetector will not be interfered with by other frequencies. The index $hr_1$ generated from the signal of $2^N$ points after the FFT is the index of the present heart rate ($hr_L$), the index of the previous heart rate ($hr_P$) is recorded as a new index $hr_1$, and then the initial mode switches to the rest mode.

It is noted that because the data for detecting the heart rate are generated over time, a present heart rate for a specific time is determined within each frame. The two parameters $hr_L$ and $hr_P$ used in this embodiment are defined based on the result observed at a specific time, and will change according to the various observation times. For instance, if the specific observation time is at frame #3, the present heart rate for frame #3 is $hr_L$, and the heart rate for frame #2 (i.e. the previous heart rate for frame #3) is $hr_P$. If the specific observation time is at frame #2, the present heart rate for frame #2 is $hr_L$, and the heart rate for frame #1 (the previous heart rate for frame #2) is $hr_P$.

The rest mode: There is also no interference from other frequencies because of the rest mode, and thus the new index $hr_1$ generated from the new frame is $hr_L$. When the user wears a heart rate detection device on his/her wrist and bends his/her fingers in a slight motion condition (such as pressing the keys of a keyboard or writing on a paper), the motion signals cannot be detected by the G-sensor, the GR'={ø}. However, bending the fingers may cause the skin of the fingers to undulate, and the detected PPG signal has no characteristics of the harmonic frequency at this moment (i.e. it does not conform with equation (1)). This situation is called the slight motion mode, and the obtained index $hr_1$ at this moment may be the index of the frequency of the bending fingers rather than the index of the heart rate. To obtain the correct heart rate, a search range Δs is defined, preferably, Δs=2, and equation (3) is used to trace the present heart rate ($hr_L$).

$$hr_L = \begin{cases} hr_1, |hr_P - hr_1| \leq \Delta s \\ hr_2, |hr_P - hr_2| \leq \Delta s \\ hr_3, |hr_P - hr_3| \leq \Delta s \\ hr_4, |hr_P - hr_4| \leq \Delta s \\ hr_P, \text{otherwise} \end{cases} \quad (3)$$

For example, when GR'={ø}, HR'=$hr_1$, $hr_2$, $hr_3$, $hr_4$=20, 24, 42, 18 if $hr_P$=23. Because the GR' is an empty set, it is understood that the user is in the slight motion mode, and the index $hr_i$ is not the index $hr_L$ at this moment. A correct $hr_L$=24 is determined using Equation (3). The correct heart rate can still be tracked using the above-mentioned method even if the spectral signal is distorted.

In step 240 of FIG. 2, a present heart rate is obtained by an interval tracking algorithm using the first heart rate and the plurality of sport intervals generated from the different sampling time intervals, and the description is illustrated in the next paragraph.

Figure 8A:
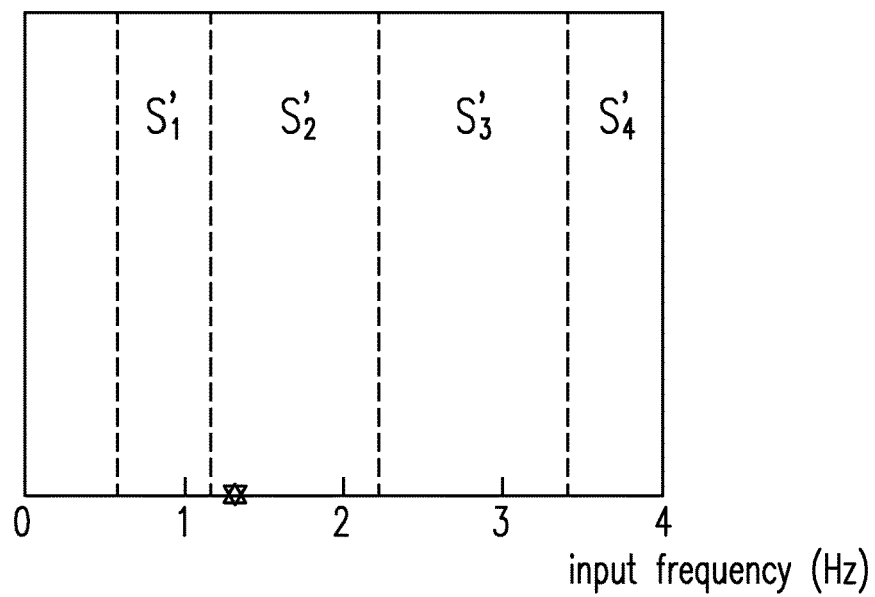
FIGS. 8(*a*) and 8(*b*) are schematic diagrams showing the sport intervals according to the first embodiment in the present invention.
Figure 8B:
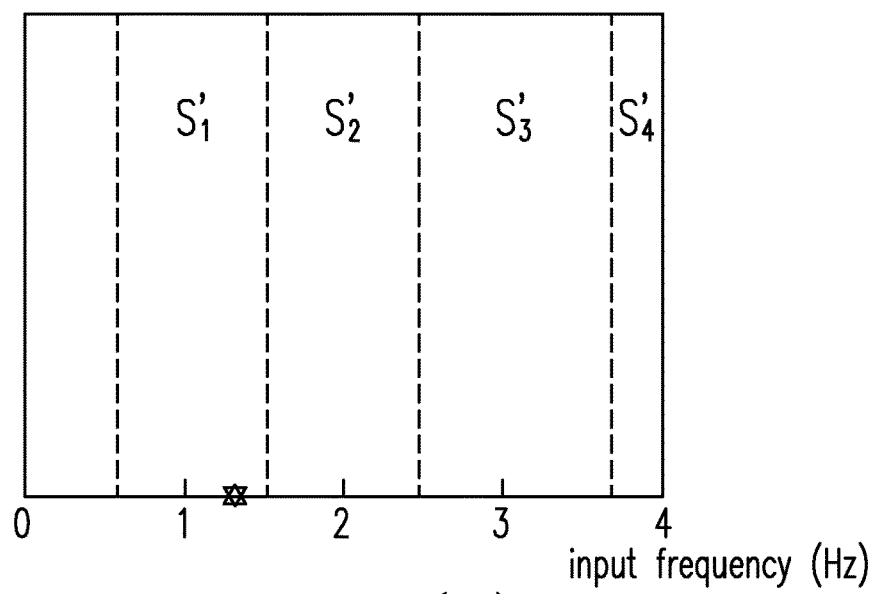

The sport mode: The photodector may produce a lot of statistical noise because of the movement of the human body during exercise, and thus the present heart rate cannot be obtained directly from the PPG spectrum. To obtain the correct heart rate, $S'_P \in S$ is defined as a sport interval where the index $hr_L$ for the previous frame is situated, and $S'_P$ is the $P^{th}$ interval for the previous frame; and $S'_L \in S$ is defined as a sport interval where the index $hr_P$ for the present frame is situated, and $S'_L$ is the $L^{th}$ interval of the present frame. For example, FIGS. 8(a) and 8(b) are schematic diagrams showing the sport intervals according to the first embodiment in the present invention, wherein the spectrum of the motion signals shown in FIG. 5 is used, the waveform in the spectrum and the Y-axis are removed, and the sport intervals defined by $gr_1$, $gr_2$ and $gr_3$ and the X-axis are maintained. FIG. 8(a) shows the sport intervals defined by the previous frame, and FIG. 8(b) shows the sport intervals defined by the present frame. Please refer to FIG. 8(a), if the index $hr_L$ for the previous frame is index 21 (i.e., 1.3125 Hz, or 79 heart beats per minute), the index $hr_L$ will be situated within the interval $S'_2$ (the asterisk in FIG. 8(a)), and thus $S'_P=S'_2$ and P=2. Please refer to FIG. 8(b), when the sporting state is changed to cause the change of the motion signals, the defined sport intervals will also be changed accordingly. The index $hr_P$ for the present frame is index 21 at this moment, and the index $hr_P$ is situated within the interval $S'_4$ (the asterisk in FIG. 8(b)), and thus $S'_L=S'_1$ and L=1. The stronger the sport strength the higher the corresponding heart rate will rise, and vice versa. Therefore, the present heart rate is obtained according to the relationship between the sport mode of the human body and his/her heart rate in the present invention. The relationship between the present heart rate and the sport intervals can be grouped as the following cases:

Case 1: When P=L, a. find the index set HR" from HR' set, the index $hr_i \in S'_L$ in the present frame; and b. select the index $hr_i$ (which is the closest to $hr_P$ among the index set HR") from HR", wherein the index $hr_i$ must satisfy the condition of $\{|hr_i - hr_P| \leq \Delta s\}$, and $hr_i$ is the index of the present heart rate.

Case 2: When P>L, a. find the index set HR" from HR' set, the index $hr_i \in S'_L \cup S'_{L+1}$ and $\geq hr_P$ in the present frame; and b. select the index $hr_i$ (which is the closest to $hr_P$ among the index set HR") from HR", wherein the index $hr_i$ must satisfy the condition of $\{|hr_i - hr_P| \leq \Delta s\}$, and $hr_i$ is the index of the present heart rate.

Case 3: When P<L, a. find the index set HR" from HR' set, the index $hr_i \in S'_L \cup S'_{L-1}$ and $\leq hr_P$ in the present frame; and b. select the index $hr_i$ (which is the closest to $hr_P$ among HR") from HR", wherein the $hr_i$ must satisfy the condition of $\{|hr_i - hr_P| \leq \Delta s\}$ and $hr_i$ is the index of the present heart rate.

Case 4: If HR"=$\{\emptyset\}$ or $\{|hr_i - hr_P| \Delta s\} = \{\emptyset\}$ in any one of Cases 1 to 3, it means that the PPG is affected by the non-regular motion signals (such as viewing the watch, wiping sweat or waving hands) and the non-regular motion signals may cause the loss of the heart rate signals. Because a human heart rate during exercise is approximately the same as the frequency of one pace of the two legs (where the frequency corresponds to $gr_2$), the rising or descending trend for the heart rate can be estimated according to equation (4).

$$\begin{cases} hr_L \uparrow, & gr2 > hr_P \\ hr_L \downarrow, & gr2 < hr_P \\ hr_L = hr_P, & gr2 = hr_P \end{cases} \quad (4)$$

The scopes $E_{23}$ and $E_{12}$ obtained from equation (2) are used to deduce the variable that $hr_L$ needs to be adjusted. When $hr_L \uparrow$, equation (5) is applicable.

$$hr_L = \begin{cases} hr_P + 3, & 4 \geq \frac{E_{12}}{E_{23}} \geq 3 \\ hr_P + 2, & 3 \geq \frac{E_{12}}{E_{23}} \geq 2 \\ hr_P + 1, & 2 \geq \frac{E_{12}}{E_{23}} \geq 0 \\ hr_P, & \text{otherwise} \end{cases} \quad (5)$$

When $hr_L \downarrow$, equation (6) is applicable.

$$hr_L = \begin{cases} hr_P - 3, & 4 \geq \frac{E_{12}}{E_{23}} \geq 3 \\ hr_P - 2, & 3 \geq \frac{E_{12}}{E_{23}} \geq 2 \\ hr_P - 1, & 2 \geq \frac{E_{12}}{E_{23}} \geq 0 \\ hr_P, & \text{otherwise} \end{cases} \quad (6)$$

To better define the method for detecting the heart rate in the present invention, the following are the experimental data:

Frame #0   HR' = 22, 25, 19, 42   GR' = 0, 0, 0   $hr_P$ = 22   $hr_L$ = 22
Frame #0 is at the initial mode, and $hr_1$ is the present heart rate $hr_L$.
Frame #1   HR' = 22, 43, 18, 20   GR' = 0, 0, 0   $hr_P$ = 22   $hr_L$ = 22
After the initial mode, the rest mode starts at frame #1 and GR' = $\{\emptyset\}$.
Whether $hr_1$ is closest to $hr_P$ is determined using equation (3), and thus $hr_L = hr_1 = 22$.
. . .
Frame #5   HR' = 23, 19, 42, 16   GR' = 16, 31, 46   $hr_P$ = 23   $hr_L$ = 23
Frame #6   HR' = 21, 24, 42, 18   GR' = 16, 31, 46   $hr_P$ = 23   $hr_L$ = 24
Because GR' $\neq \{\emptyset\}$, the sport mode starts at frame #5.
The index $hr_L$ for frame #5 is situated within $S'_2$, and thus $S'_P = S'_2$.
Furthermore, the index $hr_P$ for frame #6 is also situated within $S'_2$, and thus $S'_L = S'_2 = S'_P$. Using the method described in Case 1, HR" = 18, 21, 24 and $hr_L$ = 24.
. . .
Frame #222   HR' = 44, 26, 23, 42   GR' = 22, 45, 64   $hr_P$ = 23   $hr_L$ = 23
Frame #223   HR' = 44, 25, 42, 22   GR' = 23, 44, 64   $hr_P$ = 23   $hr_L$ = 25
The index $hr_L$ for frame #222 is situated within $S'_2$, and thus $S'_P = S'_2$.
The index $hr_P$ for frame #223 is situated within $S'_1$, and thus $S'_L = S'_1$ and P > L. Using the method described in Case 2, HR" = 25, 42, 44 and $hr_L$ = 25.
. . .
Frame #389   HR' = 27, 13, 40, 49   GR' = 14, 28, 40   $hr_P$ = 28   $hr_L$ = 27
Frame #390   HR' = 25, 13, 28, 40   GR' = 13, 26, 39   $hr_P$ = 27   $hr_L$ = 25
The $hr_L$ for frame #389 is situated within $S'_2$, and thus $S'_P = S'_2$. The index $hr_P$ for frame #390 is situated within $S'_3$, and $S'_L = S'_3$ and P < L. Using the method described in Case 3, HR" = 13, 25, 28 and $hr_L$ = 25.
. . .

Figure 9:
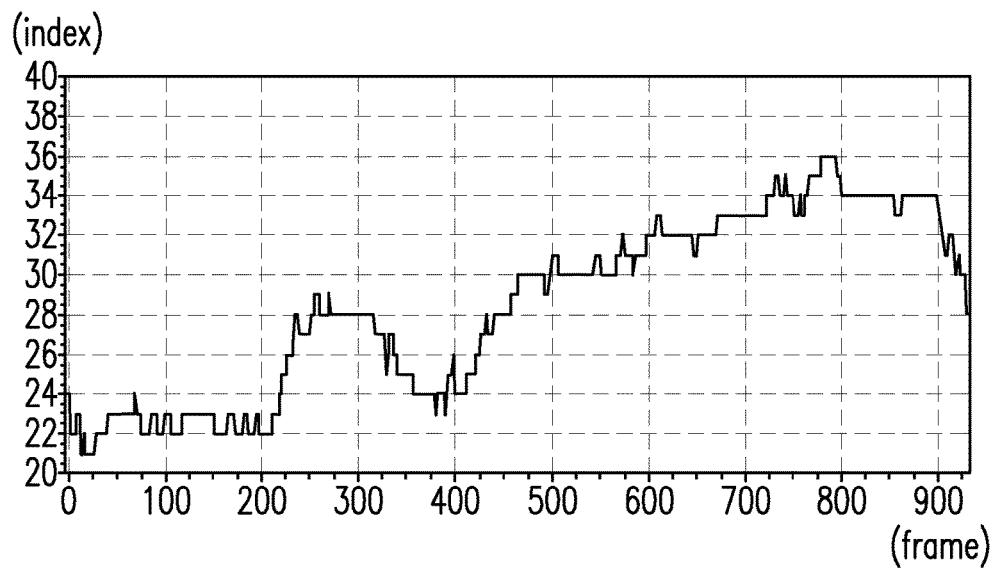
FIG. 9 is the result of the heart rate detected by the conventional electrocardiography (ECG) method.
Figure 10:
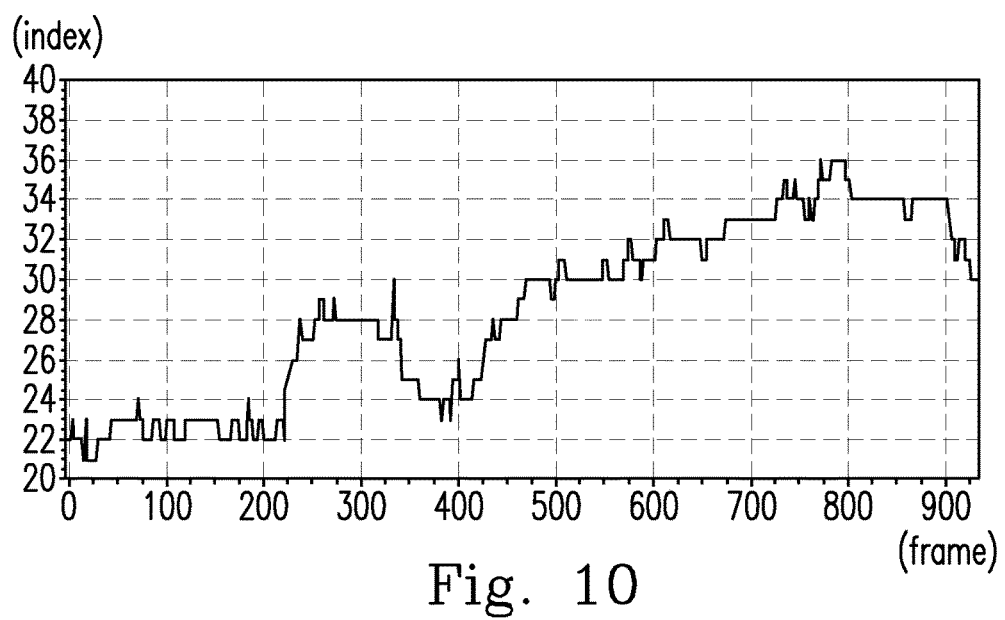
FIG. 10 is the result of the heart rate detected by the method for detecting a heart rate according to the first embodiment in the present invention.

Please refer to FIGS. 9 and 10, which show the heart rates of one user detected by different methods. FIG. 9 shows the heart rate detected by the conventional ECG method. A skilled person in the art knows that the ECG is one of the most accurate methods for detecting the heart rate in the conventional techniques. FIG. 10 shows the heart rate detected by the method for detecting a heart rate in the present invention. According to the experimental results described in the previous paragraph [0036] and comparing FIG. 9 with FIG. 10, it can be seen that the heart rate detected by the method in the present invention still is very accurate without distortion even during sports.

Based on the above, the present invention discloses a method for detecting the heart rate. A plurality of sport intervals are defined by the fundamental frequency and the harmonic frequencies of the motion signal during exercise, and the sport interval where the heart rate is located can be figured out according to the relationship between the human sport activity mode and the heart rate, and then the present heart rate is obtained by applying an interval tracking algorithm. The method disclosed in the present invention can overcome the disadvantages of the distortion of the heart rate that originate from the regular or non-regular motion signals when measuring the heart rate using the PPG The wearable device where the method of the present invention is installed can precisely detect the heart rate.

Embodiments

1. A method for detecting a heart rate, including: providing a photodetector module, a motion detector and a Fast Fourier Transform (FFT) module; acquiring a first heart rate by using the photodetector module and the FFT module; sampling at different time intervals and generating a frame using the motion detector and the FFT module, wherein the frame has a first plurality of peaks and a first plurality of indexes corresponding to the first plurality of peaks, and a plurality of sport intervals are defined by the first plurality of indexes; and acquiring a present heart rate by applying an interval tracking algorithm with the first heart rate and the plurality of sport intervals generated from the sampling at different time intervals.

2. The method according to Embodiment 1, further including: measuring a photoplethysmography (PPG) using the photodetector module in a rest mode; and performing an FFT on the PPG to acquire the first heart rate.

3. The method according to any one of Embodiments 1-2, wherein the photodetector module includes a photodetector, a plurality of blue light-emitting diodes (LEDs), and a plurality of green LEDs.

4. The method according to any one of Embodiments 1-3, wherein the measuring step includes: using the plurality of blue LEDs and the plurality of green LEDs as a light source to emit a light; using the light to illuminate a blood vessel; receiving a light signal reflected from the blood vessel by the photodetector; and converting the light signal to a voltage signal.

5. The method according to any one of Embodiments 1-4, including: generating at least one motion signal by the motion detector in a motion mode; and performing the FFT on the at least one motion signal sampled at different time intervals to acquire at least one frame.

6. The method according to any one of Embodiments 1-5, wherein the motion detector is an accelerometer, and the at least one motion signal has a fundamental frequency and at least one harmonic frequency.

7. The method according to any one of Embodiments 1-6, wherein the step of acquiring the first heart rate includes: acquiring a spectrum by performing the FFT on the PPG, wherein the spectrum has a second plurality of peaks and a second plurality of indexes corresponding to the second plurality of peaks; and arranging the second plurality of indexes according to their peak values, and putting the second plurality of indexes into a set, wherein a first frequency index arranged in a first place of the set is the first heart rate.

8. The method according to any one of Embodiments 1-7, further including: measuring a heart rate spectrum having a third plurality of peaks with the photodetector in sporting, wherein the heart rate spectrum has a second frequency index, a third frequency index and a fourth frequency index respectively corresponding to three of the third plurality of peaks, and the interval tracking algorithm includes: defining an $S_P$ interval as the sport interval where the first heart rate of a prior frame is located, wherein the $S_P$ interval is the $P^{th}$ sport interval of the plurality of sport intervals of the prior frame; defining an $S_L$ interval as the sport interval where the first heart rate of a present frame is located, wherein the $S_L$ interval is the $L^{th}$ sport interval of the plurality of sport intervals of the present frame; and when P=L, selecting a frequency corresponding to the second frequency index located in the $S_L$ interval as the present heart rate, wherein the second frequency index is closest among the second to fourth frequency indexes to the first frequency index.

9. The method according to any one of Embodiments 1-8, wherein the interval tracking algorithm further includes: when P>L, selecting a frequency corresponding to the third frequency index located in one of the $S_L$ interval and an $S_{L+1}$ interval as the present heart rate, wherein the third frequency index is larger than and closest among the second to fourth frequency indexes to the first frequency index.

10. The method according to any one of Embodiments 1-9, wherein the interval tracking algorithm further includes: when P<L, selecting a frequency corresponding to the fourth frequency index located in one of the $S_L$ interval and an $S_{L-1}$ interval as the present heart rate, wherein the fourth frequency index is smaller than and closest among the second to fourth frequency indexes to the first frequency index.

11. The method according to any one of Embodiments 1-10, wherein the frame has a frequency range of 0.5 Hz~4 Hz.

12. A method for detecting a heart rate, including: acquiring a motion signal of a sporter; acquiring a first heart rate from a first heart rate spectrum of the sporter at a first time interval and a second heart rate spectrum of the sporter at a second time interval, wherein the second heart rate spectrum has a first plurality of peaks and a first plurality of indexes corresponding to the first plurality of peaks; acquiring a frame of the motion signal at the second time interval, wherein the frame has a second plurality of peaks; defining the second plurality of peaks with a second plurality of indexes, and marking a first position corresponding to the first heart rate; and selecting a peak from the first plurality of peaks corresponding to a plurality of positions of the second plurality of indexes as a second heart rate, wherein the peak has a specific mathematical relationship with the first position.

13. The method according to Embodiment 12, wherein the plurality of positions are in a frequency range of 0.5 Hz~4 Hz of the frame and defined by the second plurality of indexes.

14. The method according to any one of Embodiments 12-13, further including: acquiring a first frame of the motion signal at the first time interval, wherein the first frame has a third plurality of peaks; and defining the third plurality of peaks with a third plurality of indexes, wherein the specific mathematical relationship includes: defining an $S_P$ interval as one of a first plurality of sport intervals defined by the second plurality of indexes, wherein the first position is located in the $S_P$ interval and the $S_P$ interval is the $P^{th}$ sport interval of the first plurality of sport intervals; defining an $S_L$ interval as one of a second plurality of sport intervals defined by the third plurality of indexes, wherein the first position is located in the $S_L$ interval and the $S_L$ interval is the $L^{th}$ sport interval of the second plurality of sport intervals; and when P=L, selecting a frequency corresponding to the peak of the first plurality of peaks located in the $S_L$ interval as the second heart rate, wherein the second heart rate is closest among the first plurality of indexes to the first heart rate.

15. The method according to any one of Embodiments 12-14, further including: when P>L, selecting a frequency corresponding to the peak of the first plurality of peaks located in one of the $S_L$ interval and an $S_{L+1}$ interval as the second heart rate, wherein the second heart rate is larger than and closest among the first plurality of indexes to the first heart rate.

16. The method according to any one of Embodiments 12-15, further including: when P<L, selecting a frequency corresponding to the peak of the first plurality of peaks located in one of the $S_L$ interval and an $S_{L-1}$ interval as the second heart rate, wherein the second heart rate is smaller than and closest among the first plurality of indexes to the first heart rate.

17. A method for detecting a heart rate, including: acquiring a first heart rate from a first heart rate spectrum of a sporter at a first time interval and a second heart rate spectrum of the sporter at a second time interval, wherein the second heart rate spectrum has a first plurality of peaks and a first plurality of indexes corresponding to the first plurality of peaks; marking the first heart rate in a first position of a first plurality of frequency intervals; and selecting a specific peak from the first plurality of peaks, which has a specific mathematical relationship with the first position, and is a second heart rate.

18. The method according to Embodiment 17, further including: acquiring a motion signal of the sporter; acquiring a first frame of the motion signal at the first time interval, wherein the first frame has a second plurality of peaks and a second plurality of frequency intervals are defined by the second plurality of peaks; and acquiring a second frame of the motion signal at the second time interval, wherein the second frame has a third plurality of peaks and the first plurality of frequency intervals are defined by the third plurality of peaks.

19. The method according to any one of Embodiments 17-18, wherein the specific mathematical relationship includes: defining an $S_P$ interval as one of the second plurality of frequency intervals, wherein the first position is located in the $S_P$ interval and the $S_P$ interval is the $P^{th}$ interval of the second plurality of frequency intervals; defining an $S_L$ interval as one of the first plurality of frequency intervals, wherein the first position is located in the $S_L$ interval and the $S_L$ interval is the $L^{th}$ interval of the first plurality of frequency intervals; when P=L, selecting the frequency corresponding to the specific peak of the first plurality of peaks located in the $S_L$ interval as the second heart rate, wherein the second heart rate is closest among the first plurality of indexes to the first heart rate; when P>L, selecting the frequency corresponding to the specific peak of the first plurality of peaks located in one of the $S_L$ interval and an $S_{L+1}$ interval as the second heart rate, wherein the second heart rate is larger than and closest among the first plurality of indexes to the first heart rate; and when P<L, selecting the frequency corresponding to the specific peak of the first plurality of peaks located in one of the $S_L$ interval and an $S_{L-1}$ interval as the second heart rate, wherein the second heart rate is smaller than and closest among the first plurality of indexes to the first heart rate.

20. The method according to any one of Embodiments 17-19, wherein the first frame and the second frame have a frequency range of 0.5 Hz~4 Hz.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for detecting a heart rate, comprising:
   providing a photodetector module, a motion detector and a Fast Fourier Transform (FFT) module;
   acquiring a first heart rate by using the photodetector module and the FFT module;
   after acquiring the first heart rate, sampling a signal obtained using the motion detector and generating a frame for the FFT module, wherein in the frame, there are a first plurality of peaks and a first plurality of indexes corresponding to the first plurality of peaks, and a plurality of sport intervals are defined by the first plurality of indexes; and
   acquiring a present heart rate by applying an interval tracking algorithm with the first heart rate and the plurality of sport intervals generated from the step of sampling the signal obtained using the motion detector.

2. The method as claimed in claim 1, further comprising:
   measuring a photoplethysmography (PPG) using the photodetector module in a rest mode; and
   performing an FFT on the PPG to acquire the first heart rate.

3. The method as claimed in claim 2, wherein the photodetector module comprises a photodetector, a plurality of blue light-emitting diodes (LEDs), and a plurality of green LEDs.

4. The method as claimed in claim 3, wherein the measuring step comprises:
   using the plurality of blue LEDs and the plurality of green LEDs as a light source to emit a light;
   using the light to illuminate a blood vessel;
   receiving a light signal reflected from the blood vessel by the photodetector; and
   converting the light signal to a voltage signal.

5. The method as claimed in claim 2, comprising:
   generating at least one motion signal by the motion detector in a motion mode; and
   performing the FFT on the at least one motion signal sampled to acquire at least one frame.

6. The method as claimed in claim 5, wherein the motion detector is an accelerometer, and the at least one motion signal has a fundamental frequency and at least one harmonic frequency.

7. The method as claimed in claim 2, wherein the step of acquiring the first heart rate comprises:
   acquiring a spectrum by performing the FFT on the PPG, wherein the spectrum has a second plurality of peaks and a second plurality of indexes corresponding to the second plurality of peaks; and
   arranging the second plurality of indexes according to their peak values, and putting the second plurality of indexes into a set, wherein a first frequency index arranged in a first place of the set is the first heart rate.

8. The method as claimed in claim 7, further comprising:
   measuring a heart rate spectrum having a third plurality of peaks with the photodetector during sports, wherein the heart rate spectrum has a second frequency index, a third frequency index and a fourth frequency index respectively corresponding to three of the third plurality of peaks, and the interval tracking algorithm comprises:
   defining an $S_P$ interval as the sport interval where the first heart rate of a prior frame is located, wherein the $S_P$ interval is the $P^{th}$ sport interval of the plurality of sport intervals of the prior frame;

defining an $S_L$ interval as the sport interval where the first heart rate of a present frame is located, wherein the $S_L$ interval is the $L^{th}$ sport interval of the plurality of sport intervals of the present frame; and when P=L, selecting a frequency corresponding to the second frequency index located in the $S_L$ interval as the present heart rate, wherein the second frequency index is closest among the second to fourth frequency indexes to the first frequency index.

9. The method as claimed in claim 8, wherein the interval tracking algorithm further comprises:

when P>L, selecting a frequency corresponding to the third frequency index located in one of the $S_L$ interval and an $S_{L+1}$ interval as the present heart rate, wherein the third frequency index is larger than and closest among the second to fourth frequency indexes to the first frequency index.

10. The method as claimed in claim 9, wherein the interval tracking algorithm further comprises:

when P<L, selecting a frequency corresponding to the fourth frequency index located in one of the $S_L$ interval and an $S_{L-1}$ interval as the present heart rate, wherein the fourth frequency index is smaller than and closest among the second to fourth frequency indexes to the first frequency index.

11. The method as claimed in claim 1, wherein the frame has a frequency range of 0.5 Hz~4 Hz.

12. A method for detecting a heart rate, comprising:

acquiring a motion signal of a sporter;

acquiring at a first instant a first heart rate from a first heart rate frequency spectrum of a sporter corresponding to a first time interval, and at a second instant a second heart rate frequency spectrum of the sporter corresponding to a second time interval, wherein the second heart rate frequency spectrum has a first plurality of peaks and a first plurality of indexes corresponding to the first plurality of peaks;

acquiring a frame of the motion signal at the second time interval, wherein in the frame, there is a second plurality of peaks;

defining the second plurality of peaks with a second plurality of indexes, and marking a first position corresponding to the first heart rate; and selecting a peak from the first plurality of peaks which correspond to a plurality of positions of the second plurality of indexes as a second heart rate, wherein the peak has a specific mathematical relationship with the first position.

13. The method as claimed in claim 12, wherein the plurality of positions are in a frequency range of 0.5 Hz~4 Hz of the frame and defined by the second plurality of indexes.

14. The method as claimed in claim 12, further comprising:

acquiring a first frame of the motion signal at the first time interval, wherein the first frame has a third plurality of peaks; and defining the third plurality of peaks with a third plurality of indexes, wherein the specific mathematical relationship comprises:

defining an $S_P$ interval as one of a first plurality of sport intervals defined by the second plurality of indexes, wherein the first position is located in the $S_P$ interval and the $S_P$ interval is the $P^{th}$ sport interval of the first plurality of sport intervals;

defining an $S_L$ interval as one of a second plurality of sport intervals defined by the third plurality of indexes, wherein the first position is located in the $S_L$ interval and the $S_L$ interval is the $L^{th}$ sport interval of the second plurality of sport intervals; and when P=L, selecting a frequency corresponding to the peak of the first plurality of peaks located in the $S_L$ interval as the second heart rate, wherein the second heart rate is closest among the first plurality of indexes to the first heart rate.

15. The method as claimed in claim 14, further comprising:

when P>L, selecting a frequency corresponding to the peak of the first plurality of peaks located in one of the $S_L$ interval and an $S_{L+1}$ interval as the second heart rate, wherein the second heart rate is larger than and closest among the first plurality of indexes to the first heart rate.

16. The method as claimed in claim 14, further comprising:

when P<L, selecting a frequency corresponding to the peak of the first plurality of peaks located in one of the $S_L$ interval and an $S_{L-1}$ interval as the second heart rate, wherein the second heart rate is smaller than and closest among the first plurality of indexes to the first heart rate.

17. A method for detecting a heart rate, comprising:

acquiring at a first instant a first heart rate from a first heart rate frequency spectrum of a sporter corresponding to a first time interval, and at a second instant a second heart rate frequency spectrum of the sporter corresponding to a second time interval, wherein the second heart rate frequency spectrum has a first plurality of peaks and a first plurality of indexes corresponding to the first plurality of peaks, and the first plurality of indexes define a first plurality of frequency intervals;

marking the first heart rate in a first position of the first plurality of frequency intervals; and selecting a specific peak from the first plurality of peaks, which has a specific mathematical relationship with the first position, and is a second heart rate.

18. The method as claimed in claim 17, further comprising:

acquiring a motion signal of the sporter;

acquiring a first frame of the motion signal at the first time interval, wherein the first frame has a second plurality of peaks and a second plurality of frequency intervals are defined by the second plurality of peaks; and acquiring a second frame of the motion signal at the second time interval, wherein the second frame has a third plurality of peaks and the first plurality of frequency intervals are defined by the third plurality of peaks.

19. The method as claimed in claim 18, wherein the specific mathematical relationship comprises:

defining an $S_P$ interval as one of the second plurality of frequency intervals, wherein the first position is located in the $S_P$ interval and the $S_P$ interval is the $P^{th}$ interval of the second plurality of frequency intervals;

defining an $S_L$ interval as one of the first plurality of frequency intervals, wherein the first position is located in the $S_L$ interval and the $S_L$ interval is the $L^{th}$ interval of the first plurality of frequency intervals;

when P=L, selecting the frequency corresponding to the specific peak of the first plurality of peaks located in the $S_L$ interval as the second heart rate, wherein the second heart rate is closest among the first plurality of indexes to the first heart rate;

when P>L, selecting the frequency corresponding to the specific peak of the first plurality of peaks located in one of the $S_L$ interval and an $S_{L+1}$ interval as the second heart rate, wherein the second heart rate is larger than and closest among the first plurality of indexes to the first heart rate; and when P<L, selecting the frequency corresponding to the specific peak of the first plurality of peaks located in one of the $S_L$ interval and an $S_{L-1}$ interval as the second heart rate, wherein the second heart rate is smaller than and closest among the first plurality of indexes to the first heart rate.

20. The method as claimed in claim 18, wherein the first frame and the second frame have a frequency range of 0.5 Hz~4 Hz.

\* \* \* \* \*